United States Patent [19]

Burg et al.

[11] Patent Number: 5,380,894

[45] Date of Patent: Jan. 10, 1995

[54] PRODUCTION OF HYDROXY FATTY ACIDS AND ESTOLIDE INTERMEDIATES

[75] Inventors: Douglas A. Burg, Easton, Pa.; Robert Kleiman; Selim M. Erhan, both of Peoria, Ill.

[73] Assignee: The United States of America as represented by the Secretary of Agriculture, Washington, D.C.

[21] Appl. No.: 662,606

[22] Filed: Mar. 1, 1991

[51] Int. Cl.$^6$ ............................................. C07C 59/255

[52] U.S. Cl. .................. 554/219; 554/112; 554/223; 554/224; 554/165

[58] Field of Search ............... 554/115, 219, 223, 224, 554/165

[56] References Cited

U.S. PATENT DOCUMENTS

| | | | |
|---|---|---|---|
| 2,652,410 | 9/1953 | Cunningham et al. | 260/405 |
| 2,793,219 | 5/1957 | Barrett et al. | 562/509 |
| 2,793,220 | 5/1957 | Barrett et al. | 562/509 |

FOREIGN PATENT DOCUMENTS

| | | |
|---|---|---|
| 0194718 | 6/1986 | European Pat. Off. |
| 7204130 | 3/1972 | Netherlands |

OTHER PUBLICATIONS

S. Okumura et al., "Synthesis of Estolides During Hydrolysis of Castor Oil by *Geotrichum candidum* Lipase," Yukagaku 32(5): 271–273 (1983).

K. L. Mikolajczak et al., "Penta-Acid Triglycerides of *Chamaepeuce afra* Seed Oil," Biochim. Biophys. Acta 152: 244–254 (1968).

R. V. Madrigal et al., "Estolide Triglycerides of *Trewia nudiflora* Seed Oil," Lipids 17(9): 650–655 (1982).

R. D. Plattner et al., "Hydroxy Acids and Estolide Triglycerides of *Heliophila amplexicaulis* L.f. Seed Oil," Lipids 14(6): 576–579 (1979).

H. W. Sprecher et al., "Structure of an Optically Active Allene-Containing Tetraester Triglyceride Isolated from the Seed Oil of *Sapium sebiferum*," Biochemistry 4(9): 1856–1863 (Sep. 1965).

K. Payne-Wahl et al., "Quantitation of Estolide Triglycerides in Sapium Seed by High Performance Liquid Chromatography with Infrared Detection" J. Am. Oil Chem. Soc. 60(5): 1011–1012 (May 1983).

R. W. Johnson, "Dimerization and Polymerization," In Fatty Acids, E. H. Pryde (ed.), AOCS (1979), pp. 343–352.

E. C. Leonard, "Dimer Acids," In Encyclopedia of Chemical Technology, Kirk-Othmer, 3rd edition, vol. 7, pp. 768–772, John Wiley & Sons (1979).

Johnson, AOCS, pp. 343–352 1979.

Tullock et al, Phytochemistry, vol. 20, No. 12, pp. 2711–2716, 1981.

Lakshominaroyana et al, Journal of the American Oil Chemist, vol. 59, No. 5, pp. 238–240, 1982.

Yamaguche et al, Chemical Abstracts, vol. 110, No. 21, p. 612, 1989, 191515f.

Primary Examiner—José G. Dees
Assistant Examiner—Deborah Carr
Attorney, Agent, or Firm—M. Howard Silverstein; Randall E. Deck; John D. Fado

[57] ABSTRACT

A process for the production of hydroxy fatty acids and novel estolide compounds, each of which may be used as lubricants, greases, plasticizers and printing inks, as well as in cosmetics. The estolides are of the formula (I):

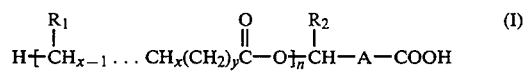

wherein $R_1$ is selected from $C_6$–$C_{16}$ hydrocarbons which may be saturated or unsaturated, and branched or straight chain, and optionally substituted, such as with one or more hydroxy groups; $R_2$ is independently selected from $C_2$–$C_{17}$ hydrocarbons which may be saturated or unsaturated, and branched or straight chain, and optionally substituted, such as with one or more hydroxy groups; A is selected from $C_3$–$C_{14}$ hydrocarbons which may be saturated or unsaturated, and branched or straight chain, and optionally substituted; n is greater than or equal to 1; y is an integer from 3–13; x is 1 or 2; and ... designates a single or double carbon/carbon bond. Formation of these estolides is by catalytic reaction of unsaturated fatty acids, especially $\Delta^5$ and $\Delta^6$ unsaturated fatty acids. Following their formation, the estolides may be recovered for subsequent use, or in the alternative, they may be hydrolyzed to produce hydroxy fatty acids.

22 Claims, No Drawings

PRODUCTION OF HYDROXY FATTY ACIDS AND ESTOLIDE INTERMEDIATES

BACKGROUND OF THE INVENTION

1. Field of the Invention

This invention relates to hydroxy fatty acids, a process for their production, and estolide intermediates. The hydroxy fatty acids and estolides are useful as lubricants, greases, plasticizers and printing inks, as well as in cosmetics.

2. Description of the Prior Art

Unsaturated fatty acids have been used in the past for the production of dimer acids by a variety of techniques, including clay catalyzed reactions, as reviewed by Johnson ["Dimerization and Polymerization," in: *Fatty Acids*, E. H. Pryde (ed.), AOCS, (1979), pages 343-352] and Leonard [in: *Encyclopedia of Chemical Technology*, Kirk-Othmer, John Wiley & Sons, third edition, volume 7, (1979)]. Depending upon the fatty acid feed, the dimer acids were produced together with monomer acids, and ranged in structure from acyclic to monocyclic to polycyclic. In accordance with the goals of these prior art processes, reaction conditions were selected to maximize yields of these dimer acids. No estolides have been reported or identified as products of any of these previous methods.

Yamaguchi et al. [Japanese Patent No. 213,387, (1990)] recently described a process for enzymatic production of estolides from hydroxy fatty acids present in castor oil using lipase. However, such estolides would be composed of esters at the 12 carbon of the fatty acids.

Hydroxy fatty acids have also been described, and are useful as lubricants and greases and in cosmetics. However, there is no domestic commercial source of hydroxy fatty acids currently available. The hydroxy fatty acids are derived from castor oil which must be imported.

SUMMARY OF THE INVENTION

We have now invented a process for the production of hydroxy fatty acids and novel estolide compound, each of which may be used as lubricants, greases, plasticizers and printing inks, as well as in cosmetics. The estolides are of the formula (I):

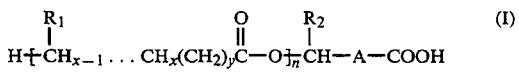
(I)

wherein $R_1$ is selected from $C_6-C_{16}$ hydrocarbons which may be saturated or unsaturated, and branched or straight chain, and optionally substituted, such as with one or more hydroxy groups; $R_2$ is independently selected from $C_2-C_{17}$ hydrocarbons which may be saturated or unsaturated, and branched or straight chain, and optionally substituted, such as with one or more hydroxy groups; A is selected from $C_3-C_{14}$ hydrocarbons which may be saturated or unsaturated, and branched or straight chain, and optionally substituted; n is greater than or equal to 1; y is an integer from 3-13; x is 1 or 2; and ... designates a single or double carbon/carbon bond. Formation of these estolides is by catalytic reaction of unsaturated fatty acids. Following their formation, the estolides may be recovered for subsequent use, or in the alternative, they may be hydrolyzed to produce hydroxy fatty acids.

In accordance with this discovery, it is an object of this invention to provide novel estolide compounds having utility as lubricants, greases, plasticizers and printing inks.

It is a further object of this invention to provide a method of making these estolide compounds and also hydroxy fatty acids having utility as lubricants, greases, plasticizers and printing inks, as well as in cosmetics.

Other objects and advantages of this invention will become readily apparent from the ensuing description.

DETAILED DESCRIPTION

Starting materials for use in the invention include one or a mixture of unsaturated fatty acids of the formula (II):

(II)

wherein R is selected from $C_6-C_{16}$ hydrocarbons which may be saturated or unsaturated, and branched or straight chain, and z is 3-13. Exemplary unsaturated fatty acid starting materials include but are not limited to $\Delta^{13}$ unsaturated fatty acids such as erucic acid (22:1 $\Delta^{13}$), $\Delta^9$ unsaturated fatty acids such as oleic acid (18:1 $\Delta^9$) and palmitoleic acid (16:1 $\Delta^9$), $\Delta^6$ unsaturated fatty acids such as petroselinic acid (16:1 $\Delta^6$), and especially $\Delta^5$ unsaturated fatty acids. Without being limited thereto, preferred $\Delta^5$ unsaturated fatty acids include 5-docosenoic acid (22:1 $\Delta^5$), 5,13-docosadienoic acid (22:2 $\Delta^{5,13}$), 18:1 $\Delta^5$ fatty acids, and especially 5-eicosenoic acid (20:1 $\Delta^5$).

The $\Delta^5$ and other unsaturated fatty acids are naturally occurring in a variety of plant oils and may be conveniently obtained for use therefrom. Meadowfoam oil, having a high content of $\Delta^5$ unsaturated fatty acids (total fatty acids composed of approximately 60% 5-eicosenoic acid, 10% 5-docosenoic acid, 19% 5,13-docosadienoic acid, and less than 5% 18:1 $\Delta^5$ fatty acids), is particularly preferred as a source of the starting material. However, the practitioner skilled in the art will recognize that other oils may be used as sources, such as pine oils or marsh-marigold oils. As starting materials in the reaction of the invention, the unsaturated fatty acids may be provided in substantially pure form or, in the alternative, they may be provided as a mixture or in impure form, such as an above-mentioned naturally occurring oil subjected to saponification.

The novel estolide intermediates of this invention are prepared by a reaction of one or more of the unsaturated fatty acids, in the presence of a suitable catalyst and water under suitable temperature and pressure conditions effective to form an estolide of the formula (I):

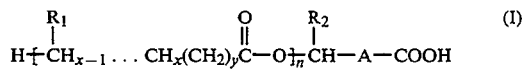
(I)

wherein $R_1$ is selected from $C_6-C_{16}$ hydrocarbons which may be saturated or unsaturated, and branched or straight chain, and optionally substituted, such as with one or more hydroxy groups; $R_2$ is independently selected from $C_2-C_{17}$ hydrocarbons which may be saturated or unsaturated, and branched or straight chain, and optionally substituted, such as with one or more hydroxy groups; A is selected from $C_3-C_{14}$ hydrocarbons which may be saturated or unsaturated, and branched or straight chain, and optionally substituted, n is greater than or equal to 1; y is an integer from 3-13;

x is 1 or 2; and ... designates a single or double carbon/-carbon bond.

Preferred estolides include those formed by reaction of the above-mentioned $\Delta^9$ unsaturated fatty acids, and especially $\Delta^6$ and $\Delta^5$ unsaturated fatty acids. In accordance with the former preferred embodiment, the estolides (I) formed are of the formula wherein $R_1$, $R_2$, A, n, y, x and ... are as described above except that $R_2$ is selected from $C_7$–$C_{17}$ hydrocarbons, A is selected from $C_3$–$C_8$ hydrocarbons, and y is an integer from 3–7.

Particularly preferred estolides formed from the $\Delta^5$ and $\Delta^6$ unsaturated fatty acids are of the formula wherein $R_1$, $R_2$, A, n, y, x and ... are as described above except that $R_1$ is selected from $C_{11}$–$C_{16}$ hydrocarbons, $R_2$ is selected from $C_{10}$–$C_{17}$ hydrocarbons, A is selected from $C_3$–$C_6$ hydrocarbons, and y is 3 or 4.

Following the reaction, the crude estolide fraction is separated from the catalyst as by filtration, and the water is removed. The estolides may be further purified by distillation to remove the low boiling monomer fraction (unsaturated fatty acids and saturated fatty acids), leaving a residue fraction containing estolides and, depending upon reaction conditions, a variable amount of dimer acids which may also be removed, for example, by chromatography or distillation. In a preferred embodiment, reaction conditions will be selected such that no or substantially no dimer acids are produced in the course of reaction, with only estolides being formed and the residue fraction comprising substantially pure estolides.

As mentioned above, the estolides may be recovered for use without further reaction, or, in the alternative, the estolides may be hydrolyzed to produce a mixture of fatty acids and hydroxy fatty acids. The fatty acids formed during hydrolysis are of the formula (III):

$$R_1-CH_{x-1}\ldots CH_x(CH_2)_yCOOH \qquad (III)$$

while the hydroxy fatty acids are of the formula (IV):

$$\begin{array}{c} \text{OH} \\ | \\ R_2-CH-A-COOH \end{array} \qquad (IV)$$

wherein $R_1$, $R_2$, A, y and x are the same as described above.

Hydrolysis of the estolides as described generally results in the formation of a plurality of hydroxy fatty acids differing in the position of the hydroxy group along the hydrocarbon chain, and in ratios varying with the particular estolide hydrolyzed. For example, upon hydrolysis, estolides formed by the reaction of $\Delta^5$ unsaturated fatty acids predominantly yield 6-hydroxy fatty acids, with smaller amounts of 5- and 7-hydroxy fatty acids also being formed. A summary of the structure of the estolides formed from reaction of a number of representative fatty acids, as well as the hydroxy fatty acids formed upon hydrolysis, is shown in Table I.

Conditions for the estolide formation reaction are ideally selected to minimize the production of dimer acids, with preferred temperature and initial pressure ranges of about 230°–250° C. and about 30–60 psi, respectively. The pressure is maintained at or above the initial pressure during the course of the reaction, and may reach a maximum of about 1000 psi. The concentrations of water and catalyst are advantageously between about 8–12 parts and about 6–8 parts, respectively, per 100 parts of the unsaturated fatty acid starting material. However, the practitioner skilled in the art will recognize that other conditions and concentrations may be selected at the expense of product yield and purity. Reactions should be conducted in sealed, stainless steel reactors under a $N_2$ or other inert gas atmosphere, and with agitation provided, for example, by internal stirrers or external rocking.

Particularly preferred reaction conditions and concentrations of reactants are selected such that the estolides formed in the course of the reaction are substantially free of dimer acids. In accordance with this best mode of the invention, about 100 parts of the unsaturated fatty acids are combined with about 10 parts water and about 8 parts clay catalyst in a reactor, under a $N_2$ atmosphere at about 60 psi, and at a temperature of about 250° C. Using these conditions and allowing the reaction to proceed with mixing for about 3 hours, with the pressure reaching 640 psi, reaction yields of 18% (estolides) have been attained from $\Delta^5$ unsaturated fatty acids.

TABLE I

| Starting Fatty Acid | | | Estolide | | | | Hydroxy Fatty Acid Product |
|---|---|---|---|---|---|---|---|
| Fatty Acid | z | R | y | $R_1$ | A | $R_2$ | from Hydrolysis |
| 1) 5-eicosenoic (20:1 $\Delta^5$) | 3 | $C_{14}$ | 3 | $C_{14}$ | $C_4$* | $C_{14}$* | 6-hydroxy eicosanoic* |
| | | | 3 | $C_{14}$ | $C_3$ | $C_{15}$ | 5-hydroxy eicosanoic |
| | | | 3 | $C_{14}$ | $C_5$ | $C_{13}$ | 7-hydroxy eicosanoic |
| 2) 5-octadecenoic (18:1 $\Delta^5$) | 3 | $C_{12}$ | 3 | $C_{12}$ | $C_4$* | $C_{12}$* | 6-hydroxy octadecanoic* |
| | | | 3 | $C_{12}$ | $C_3$ | $C_{13}$ | 5-hydroxy octadecanoic |
| | | | 3 | $C_{12}$ | $C_5$ | $C_{11}$ | 7-hydroxy octadecanoic |
| 3) 5-docosenoic (22:1 $\Delta^5$) | 3 | $C_{16}$ | 3 | $C_{16}$ | $C_4$* | $C_{16}$* | 6-hydroxy docosanoic* |
| | | | 3 | $C_{16}$ | $C_3$ | $C_{17}$ | 5-hydroxy docosanoic |
| | | | 3 | $C_{16}$ | $C_5$ | $C_{15}$ | 7-hydroxy docosanoic |
| 4) 5,13-docosadienoic (22:2 $\Delta^{5,13}$) | 3 | $C_{16}$ | 3 | $C_{16}$ | $C_4$ | $C_{16}$ | 6-hydroxy-13-docosenoic |
| | | | 3 | $C_{16}$ | $C_3$ | $C_{17}$ | 5-hydroxy-13-docosenoic |
| | | | 3 | $C_{16}$ | $C_5$ | $C_{15}$ | 7-hydroxy-13-docosenoic |
| | | | 3 | $C_{16}$ | $C_{10}$ | $C_{10}$ | 12-hydroxy-5-docosenoic |
| | | | 3 | $C_{16}$ | $C_{11}$ | $C_9$ | 13-hydroxy-5-docosenoic |
| | | | 3 | $C_{16}$ | $C_{12}$ | $C_8$ | 14-hydroxy-5-docosenoic |
| 5) petroselinic *18:1 $\Delta^6$) | 4 | $C_{11}$ | 4 | $C_{11}$ | $C_4$* | $C_{12}$* | 6-hydroxy octadecanoic* |
| | | | 4 | $C_{11}$ | $C_5$* | $C_{11}$* | 7-hydroxy octadecanoic* |
| | | | 4 | $C_{11}$ | $C_5$* | $C_{11}$* | 5-hydroxy octadecanoic |
| | | | 4 | $C_{11}$ | $C_6$ | $C_{10}$ | 8-hydroxy octadecanoic |
| 6) oleic (18:1 $\Delta^9$) | 7 | $C_8$ | 7 | $C_8$ | $C_7$* | $C_9$* | 9-hydroxy octadecanoic* |
| | | | 7 | $C_8$ | $C_8$* | $C_8$* | 10-hydroxy octadecanoic* |
| | | | 7 | $C_8$ | $C_5$ | $C_{11}$ | 7-hydroxy octadecanoic |
| | | | 7 | $C_8$ | $C_6$ | $C_{10}$ | 8-hydroxy octadecanoic |
| | | | 7 | $C_8$ | $C_9$ | $C_7$ | 11-hydroxy octadecanoic |

TABLE I-continued

| Starting Fatty Acid | | | Estolide | | | Hydroxy Fatty Acid Product |
|---|---|---|---|---|---|---|
| Fatty Acid | z | R | y | $R_1$ | A | $R_2$ | from Hydrolysis |
| 7) palmitoleic (16:1 $\Delta^9$) | 7 | $C_6$ | 7 | $C_6$ | $C_6$* | $C_8$* | 8-hydroxy hexadecanoic* |
| | | | 7 | $C_6$ | $C_5$ | $C_9$ | 7-hydroxy hexadecanoic |
| | | | 7 | $C_6$ | $C_7$ | $C_7$ | 9-hydroxy hexadecanoic |
| 8) erucic (22:1 $\Delta^{13}$) | 11 | $C_8$ | 11 | $C_8$ | $C_9$ | $C_{11}$ | 11-hydroxy docosanoic |
| | | | 11 | $C_8$ | $C_{10}$ | $C_{10}$ | 12-hydroxy docosanoic |
| | | | 11 | $C_8$ | $C_{11}$* | $C_9$* | 13-hydroxy docosanoic* |
| | | | 11 | $C_8$ | $C_{12}$ | $C_8$ | 14-hydroxy docosanoic |

*Predominant estolide(s) and/or hydroxy fatty acids formed.

Hydrolysis of the estolides to the fatty acids and hydroxy fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: *Official and Tentative Methods of the American Oil Chemist's Society*, third edition, AOCS, Chicago, Ill., (1973)]. Other conventional techniques including splitting with steam under pressure are contemplated as being effective. Methyl esters of the estolides and the hydroxy fatty acids, respectively, may also be formed by first treatment of the estolide with diazomethane, followed by a second treatment with sodium methoxide in methyl alcohol.

A variety of suitable catalysts may be used, particularly clay catalysts including but not limited to Montmorillonite K 10 clay, bentonite, and Filtrol Grade 13 (Fluka Chemical & Biochemical Co.,, Ronkonkoma, N.Y.).

EXAMPLE b 1

Meadowfoam oil having a composition as described above was obtained from the Oregon Meadowfoam Growers Association (SE. Salem, OR) and split by high pressure steam to obtain the fatty acids. Reactions were run at 250 C. in a 0.5-L high-pressure bomb reactor under an initial pressure of 60 psi $N_2$. The bomb was loaded with about 20 g Montmorillonite K 10 clay catalyst (Aldrich Chem., Milwaukee, Wis.), 25 g water, and then about 250 g of Meadowfoam fatty acids, and placed in a rocker to stir the contents during the reaction, which was run for 3 hr. After the reaction had cooled to room temperature, the contents were dissolved in hexane (3×100 ml) and removed from the reactor. Removal of the clay was accomplished by filtration of the reaction mixture on a Buchner funnel using Whatman (Maidstone, England) #54 filter paper (fast, hardened). The filtrate was then dried over $MgSO_4$ to remove residual water, and filtered through a Buchner funnel with a medium porosity glass frit. The remaining filtrate was composed of a mixture of estolides in combination with monomeric components ($\Delta^5$ unsaturated fatty acids) and diacids.

Initial purification of the filtrate for the removal of a substantial portion of the monomeric components was achieved by distillation with heating to 160° C. at 0.3 Torr in an Aldrich Kugelrohr distillation apparatus, yielding a residue of estolides and dimer acids. The yield for the reaction was 21% [calculated as % residue = 100% × residue wt/(residue wt + distillate wt)]. Following purification, the distillate was found to be composed of 62% estolides as determined by HPLC analysis [Veazey, *J. Am. Oil Chem. Soc.*, 63:1043 (1986)] coupled with an evaporative light-scattering detector [Barnhorst et al., paper E2 presented at the Annual American Oil Chemists' Society Meeting, Cincinnati, Ohio, May 1989].

It is understood that the foregoing detailed description is given merely by way of illustration and that modifications and variations may be made therein without departing from the spirit and scope of the invention.

We claim:

1. An estolide compound of the formula:

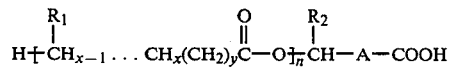

wherein $R_1$ is selected from $C_{11}$-$C_{16}$ hydrocarbons which may be saturated or unsaturated, and branched or straight chain; $R_2$ is independently selected from $C_{10}$-$C_{17}$ hydrocarbons which may be saturated or unsaturated, and branched or straight chain; A is selected from $C_3$-$C_6$ hydrocarbons which may be saturated or unsaturated, and branched or straight chain; y is 3 or 4.; n is greater than or equal to 1; x is 1 or 2; and ... designates a single or double carbon/carbon bond.

2. A compound as described in claim 1, wherein A is a $C_4$ hydrocarbon which may be saturated or unsaturated, and branched or straight chain, and n is one.

3. A compound as described in claim 2, wherein $R_1$ and $R_2$ are $C_{14}$, straight chain, saturated hydrocarbons.

4. A compound as described in claim 1, wherein A is a $C_5$ hydrocarbon which may be saturated or unsaturated, and branched or straight chain, and n is one.

5. A compound as described in claim 1, wherein A is a $C_3$ hydrocarbon which may be saturated or unsaturated, and branched or straight chain, and n is one.

6. A compound as described in claim 1, wherein one or both of $R_1$ and $R_2$ are substituted with one or more hydroxy groups.

7. A method of making estolide compounds comprising the steps of:

a. reacting one or a mixture of unsaturated fatty acids of the formula (I):

wherein R is selected from $C_6$-$C_{16}$ hydrocarbons which may be saturated or unsaturated, and branched or straight chain, and z is an integer from 3-13, in the presence of a suitable catalyst and water at a concentration between about 8 to 12 parts water per 100 parts of said unsaturated fatty acids and under suitable conditions effective to form one or more estolides of the formula (II):

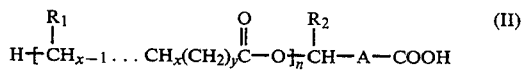
(II)

(IV)

wherein $R_1$ is selected from $C_6$–$C_{16}$ hydrocarbons which may be saturated or unsaturated, and branched or straight chain; $R_2$ is independently selected from $C_2$–$C_{17}$ hydrocarbons which may be saturated or unsaturated, and branched or straight chain; A is selected from $C_3$–$C_{14}$ hydrocarbons which may be saturated or unsaturated, and branched or straight chain; y is an integer from 3–13; n is greater than or equal to 1; x is 1 or 2; and . . . designates a single or double carbon/carbon bond; and wherein said catalyst is not a lipase; and b. separating said estolides from said catalyst and said water.

8. A method as described in claim 7 wherein z is an integer from 3–7; $R_2$ is independently selected from $C_7$–$C_{17}$ hydrocarbons which may be saturated or unsaturated, and branched or straight chain; A is a $C_3$–$C_8$ hydrocarbon which may be saturated or unsaturated, branched or straight chain; and y is an integer from 3–7.

9. A method as described in claim 8 wherein z is 3 or 4; R is selected from $C_{11}$–$C_{16}$ hydrocarbons which may be saturated or unsaturated, and branched or straight chain; $R_1$ is selected from $C_{11}$–$C_{16}$ hydrocarbons which may be saturated or unsaturated, and branched or straight chain; $R_2$ is independently selected from $C_{10}$–$C_{17}$ hydrocarbons which may be saturated or unsaturated, and branched or straight chain; A is a $C_3$–$C_6$ hydrocarbon which may be saturated or unsaturated, and branched or straight chain; and y is 3 or 4.

10. A method as described in claim 9, wherein R is a $C_{14}$ hydrocarbon, z is 3, and $R_1$ and $R_2$ are $C_{14}$ hydrocarbons, A is a $C_4$ hydrocarbon, and n is 1.

11. A method as described in claim 9, wherein R is a $C_{16}$ hydrocarbon, z is 3, and $R_1$ and $R_2$ are $C_{16}$ hydrocarbons, A is a $C_4$ hydrocarbon, and n is 1.

12. A method as described in claim 7, further comprising the steps of hydrolyzing said estolides from said step (b) to produce a reaction mixture comprising fatty acids and hydroxy fatty acids, said fatty acids being of the formula (III):

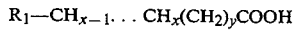 (III)

and said hydroxy fatty acids being of the formula (IV):

13. A method as described in claim 11, wherein z is an integer from 3–7; $R_2$ is independently selected from $C_7$–$C_{17}$ hydrocarbons which may be saturated or unsaturated, and branched or straight chain; A is a $C_3$–$C_8$ hydrocarbon which may be saturated or unsaturated, and branched or straight chain; and y is an integer from 3–7.

14. A method as described in claim 13 wherein z is 3 or 4; R is selected from $C_{11}$–$C_{16}$ hydrocarbons which may be saturated or unsaturated, and branched or straight chain; $R_1$ is selected from $C_{11}$–$C_{16}$ hydrocarbons which may be saturated or unsaturated, and branched or straight chain; $R_2$ is indecently selected from $C_{10}$–$C_{17}$ hydrocarbons which may be saturated or unsaturated, and branched or straight chain; A is a $C_3$–$C_6$ hydrocarbon which may be saturated or unsaturated, and branched or straight chain; and y is 3 or 4.

15. A method as described in claim 14, wherein R is a $C_{14}$ hydrocarbon, z is 3, and $R_1$ and $R_2$ are $C_{14}$ hydrocarbons, A is a $C_4$ hydrocarbon, and n is 1.

16. A method as described in claim 14, wherein R is a $C_{16}$ hydrocarbon, z is 3, and $R_1$ and $R_2$ are $C_{16}$ hydrocarbons, A is a $C_4$ hydrocarbon, and n is 1.

17. A method as described in claim 7, wherein said catalyst is clay.

18. A method as described in claim 7, wherein said step of reacting is at a temperature between about 230°–250° C. and an initial pressure between about 30 and 60 psi, and the concentration of said catalyst is between about 6–8 parts per 100 parts of said unsaturated fatty acids.

19. A method as described in claim 17, wherein said temperature is about 250° C., said pressure is about 60 psi, said catalyst concentration is about 8 parts and said water concentration is about 10 parts per 100 parts of said unsaturated fatty acids.

20. A method as described in claim 7, wherein said step of reacting is conducted in a sealed reactor with agitation.

21. A method as described in claim 7, wherein said unsaturated fatty acids are selected from the group consisting of 5-eicosenoic acid, 5-docosenoic acid, 5,13-docosadienoic acid, 18:1 $\Delta^5$ fatty acids, and mixtures thereof.

22. A method as described in claim 7, further comprising the step of purifying said estolides from said step (b).

* * * * *